United States Patent [19]
Kodukula

[11] Patent Number: 5,106,511
[45] Date of Patent: Apr. 21, 1992

[54] ON-LINE BIOLOGICAL INHIBITION/TOXICITY DETECTOR

[76] Inventor: Prasad S. Kodukula, 1234 Moore Ave., Dunbar, W. Va. 25064

[21] Appl. No.: 454,902

[22] Filed: Dec. 22, 1989

[51] Int. Cl.$^5$ .............................................. C02F 3/00
[52] U.S. Cl. ..................... 210/614; 210/85; 210/96.1; 210/143; 210/195.1; 210/620; 210/739
[58] Field of Search ............. 210/614, 622, 96.1, 210/626, 620, 85, 621, 622, 195.3, 103, 195.1, 739, 746, 93, 143; 435/289, 291; 364/500, 496

[56] References Cited

U.S. PATENT DOCUMENTS

| | | | |
|---|---|---|---|
| 4,009,099 | 2/1977 | Jeris | 210/614 |
| 4,260,490 | 4/1981 | Moss et al. | 210/96.1 |
| 4,314,969 | 2/1982 | Arthur et al. | 422/68 |
| 4,329,232 | 5/1982 | McKenna | 210/614 |
| 4,643,830 | 2/1987 | Reid | 210/629 |
| 4,783,750 | 11/1988 | Smith | 210/614 |

OTHER PUBLICATIONS

Metcalf and Eddy, *Wastewater Engineering: Treatment Disposal Reuse* (1979), 2nd Edition, published by McGraw-Hill, N.Y., p. 479.

*Primary Examiner*—Robert A. Dawson
*Assistant Examiner*—Sun Uk Kim
*Attorney, Agent, or Firm*—Beveridge, DeGrandi & Weilacher

[57] ABSTRACT

This invention describes a biological inhibition/toxicity detector, which provides an early warning of a process upset due to possible inhibition/toxicity problems in biological reactors treating municipal and/or industrial wastewaters. The detector basically comprises separate means for providing two liquids in communication with a mixing tank, a spiral plug-flow reactor, two dissolved oxygen (DO) probes, a DO analyzer, a computer, and a chart recorder. Two pumps can continuously pump portions of wastewater to be tested and acclimated active biomass (mixed liquor) from a biological reactor into the mixing tank. The wastewater and biomass are mixed and oxygenated in the tank, and then continuously fed to the plug-flow reactor. The DO concentrations at the front and back ends of the plug-flow reactor are measured separately by the two DO probes. These probes send corresponding signals through a DO analyzer to a computer, which calculates the oxygen uptake rate (OUR) or the specific oxygen uptake rate (SOUR) of the biomass mixture in the plug-flow reactor based on some user input information. A chart recorder prints out the measured DO concentrations and the calculated OUR or SOUR values. By monitoring the OUR or SOUR values continuously and accompanying them with "normal" values, the device described in this invention provides an advance warning of a potential process upset in biological reactors treating municipal and/or industrial wastewaters.

24 Claims, 3 Drawing Sheets

ON-LINE BIOLOGICAL INHIBITION/TOXICITY DETECTOR

The present invention relates to a biological inhibitor/toxicity detector device.

BACKGROUND OF THE INVENTION

Industrial manufacturing facilities used for production of organic chemicals ranging from automobile wind shield fluid to agricultural pesticides generate millions of gallons of harmful liquid wastes everyday. These wastes are generally treated in wastewater treatment plants (WTPs) before they are discharged to receiving water bodies, so that they become harmless to the environment. Such plants generally consist of biological reactors, in which organic pollutants are used as food by microorganisms and converted to innocuous end products such as carbon dioxide and water. Due to their biological nature, these reactors are very sensitive to toxic substances that can enter the reactors through the influent wastewater. Such substances may inhibit or even completely arrest the biological activity in the reactors resulting in process upsets, and, consequently, in undesirable poor quality effluents. Unfortunately, the presence of such substances, especially when they are in low concentrations, is often undetected, and, therefore, prevention of introduction of these substances into the biological reactors is extremely difficult.

One of the most common ways to determine the inhibitory or toxic effects on biological activity in WTPs is by measuring the oxygen utilization or oxygen uptake rate (OUR) of the microorganisms in the biological reactors. Under normal operating conditions, a significant decrease in the OUR compared to normal levels is generally attributed to possible presence of inhibitory or toxic substances in the influent wastewater, whereas extremely high OURs reflect high biological activity. In extreme cases, OUR can instantaneously drop to zero indicating possible presence of highly toxic compound(s) in the influent. Caution should be exercised in interpreting low OUR results, because they can also be caused by low concentrations of organics in the influent. OURs are generally normalized by expressing them on the basis of unit weight of biomass. This is referred to as specific oxygen uptake rate (SOUR). Typical units for OUR and SOUR are: mg oxygen utilized/L/hour and mg oxygen utilized/g volatile suspended solids (VSS)/hour, respectively. (Note that VSS, typically expressed as g/L, is used as an indication of biomass concentration.)

The following laboratory procedure is generally used for measuring OUR:

1) Add an appropriate amount of wastewater sample to an active biomass culture from a biological reactor to form a sample mixture;

2) Measure the dissolved oxygen (DO) concentration of the mixture in a completely filled air-tight test vessel over a period of time; and 3) Calculate the OUR based on the decrease in the DO concentration of the sample mixture over the test period.

SOUR can be calculated by dividing the OUR value by the VSS concentration in the test system.

The OUR/SOUR test is thus done on a batch basis, therefore, a toxic substance can possibly enter the WTP during the time when the influent is not sampled for the laboratory test.

Another method to measure OUR is to use a submersible respirometer, such as the one described in U.S. Pat. No. 4,314,969. In this instrument, the aeration chamber of the respirometer is filled every 15-30 minutes with the wastewater, and the oxygen utilization measured by monitoring the decrease in the oxygen concentration in the air that is recirculated through the sample. In this respirometer, only the wastewater enters the aeration chamber with no provision specifically made for addition of already active and acclimated microorganisms. Also, the oxygen utilization is measured on a batch basis only every 15-30 minutes. Alternative to its use with the influent wastewater, the respirometer can also be used within the biological reactor of a WTP. However, in this case, even if the toxic effects are detected, it is only "after the fact"; the introduction of toxics into the reactor has already occurred, and, so, there is no opportunity for taking any preventive measure.

The apparatus and the method described in the invention presented here can be used (i) to detect the presence of inhibitory and toxic substances in the influents to the WTPs before they enter the biological reactors and (ii) to divert the influent flow to a temporary storage tank until such time when it is safe to feed the reactors again with the influent. This apparatus, which can be installed on line at the front end of a WTP, measures the OUR and SOUR of a given mixture of wastewater influent and active biomass that is already acclimated to the influent undergoing treatment, and prints out the results on a chart recorder. A warning alarm is given and/or the influent flow to the biological system is diverted to a temporary emergency storage tank, if dangerous levels of inhibitory or toxic substance(s) are indicated.

The apparatus proposed in this invention can also be used in association with full, pilot or laboratory scale biological reactors to:

1) determine whether increased loadings of organics in the influent (due to increase in the concentration and/or flowrate) compared to "normal" levels would be detrimental to process performance of biological reactors, thereby helping in terms of developing process control strategies;

2) investigate biological treatability and/or the effect on an existing biological reactor of a new waste stream or a test compound;

3) measure "endogenous" or background respiration rate of biomass from biological reactors; and 4) estimate, within a few minutes, organic loadings in terms of $BOD_5$, 5-day Biochemical Oxygen Demand (Note: It takes five days to obtain $BOD_5$ results), in the influents and effluents of biological reactors. In the case of full-scale WTPs, advance knowledge of influent and effluent $BOD_5$s can be used for process control and prevention of effluent permit violations, respectively.

SUMMARY OF THE INVENTION

The present invention relates to a biological inhibitor/toxicity detector device. An object of this device is to provide an early warning of process upsets due to possible inhibition/toxicity problems in biological reactors treating municipal or industrial wastewaters. Such problems are detected in a simulated reactor, which forms the core of the device, before the influent wastewater reaches the actual biological reactor, and process upsets are prevented by a warning alarm for manual or automatic diversion of influent wastewater to an emergency storage tank until such a time when normal conditions are restored.

The device presented in this invention contains a rapid mixing tank in which portions of acclimated active biomass (mixed liquor) from the actual biological reactor in the wastewater treatment plant and influent wastewater are continuously mixed and oxygenated. The mixing tank is in flow communication with a simulated biological reactor. The mixture of the biomass and the wastewater is then fed to the simulated reactor which is a spiral plug-flow reactor. The dissolved oxygen concentrations in the mixture at the front and back ends of the plug-flow reactor are continuously measured with two dissolved oxygen probes or sensors and a DO analyzer(s) electronically linked to a computer. These measurements are transmitted to the computer, which (using some user input information) calculates the OUR and SOUR of the biomass mixture in the reactor and transmits corresponding signals to a chart recorder electronically linked to the computer. When the SOUR (or OUR as desired by the user) falls below a certain preset critical level, for longer than a certain preset time period, an alarm is set off indicating a possible inhibition/toxicity problem. In addition, the computer can also trigger diversion of the influent flow to an emergency storage tank, so that the actual biological reactor is prevented from receiving inhibitory/toxic substances, thereby avoiding a possible process upset.

A description of the preferred embodiment of the invention is presented below with references being made to the accompanying drawings.

A BRIEF DESCRIPTION OF THE DRAWINGS

FIG. 3 A-C are process flow diagrams showing where the device may be located in a biological wastewater treatment system for different applications.

DESCRIPTION OF THE PREFERRED EMBODIMENT

Figure 1:
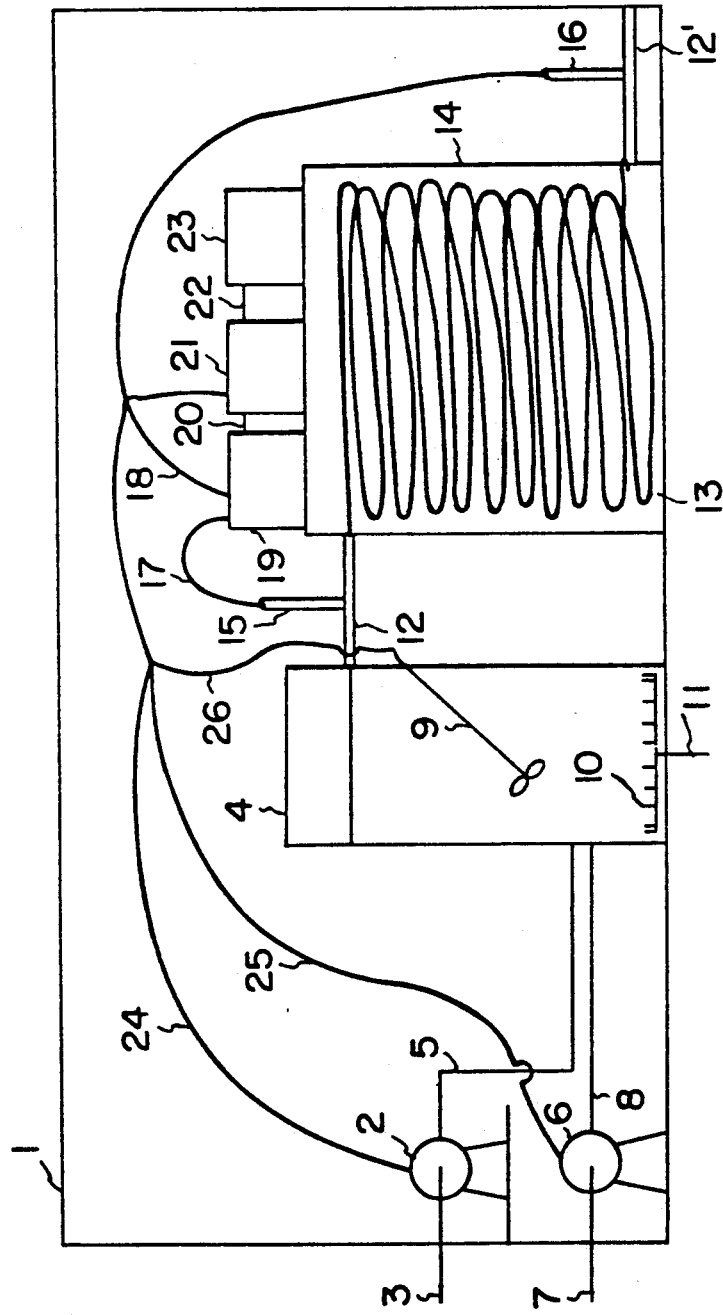
FIG. 1 is a schematic view of the preferred embodiment of the biological inhibition/toxicity detector.

The preferred embodiment of the biological inhibition/toxicity detector shown in FIG. 1 includes a housing (1) which may be generally in the shape of a box. A small water pump (2) located at the front end of the box is connected to a line (3) coming from the actual biological reactor of the wastewater treatment plant. This pump continuously pumps a small portion of acclimated active biomass from the actual biological reactor to the mixing tank (4) through a small line (5). A portion of the influent wastewater from the WTP's main influent line is drawn by another pump (6) through a water line (7) and pumped to the mixing tank through another water line (8). Alternatively, small line (5) could be connected directly to water line (8). The mixing tank is equipped with a mixer (9) and a set of diffusers (10) at the bottom, which supply oxygen to the wastewater/biomass mixture in the tank from an outside oxygen (or air) source connected through an air line (11). The wastewater mixture from the mixing tank enters, through a connecting means (12), into a plug-flow type, long, narrow, and spiral reactor (13) shown in enclosure (14) and exits from the spiral reactor via similar connecting means (12') for return of the mixture to the main influent line.

The hydraulic residence time of a wastewater mixture in the spiral reactor (13) depends on its flowrate and the volume of the reactor. A residence time in the reactor of 10 to 15 minutes is recommended. For example, a spiral reactor of gallon (3.78 liters) in volume would provide a residence time of about 15 minutes for a wastewater mixture flowrate of 250 ml/min.

The spiral reactor can be of tubular (metal material, glass or other) or flexible hose construction of about 1 inch inner diameter and about 25 feet in length, conveniently arranged in spiral form of about 1 foot spirals for a total of about 8 to 10 spiral loops. This would provide a volume of about one gallon.

There are two DO probes (or sensors), one (15) at the front end of the reactor to measure the DO concentration of the wastewater mixture as it enters the reactor and another (16) at the back end of the reactor to measure DO of the mixture as it leaves the reactor to return to the main influent line. The electrical signals from the DO probes/sensors are transmitted through different lines (17, 18) to a DO analyzer (19). (For example, Royce Instrument Corporation's Model 3060 Multichannel Analyzer With Model 60 DO sensors can be used.) The DO analyzer is in communication, through an electric line (20), with a computer (21). Based on the measured values of entrance and exit DO concentrations and the user input "reference" values of the residence time (minutes) of the wastewater/biomass mixture in the plug-flow reactor and the biomass concentration (expressed as volatile suspended solids in g/L), the computer calculates the SOUR of the biomass mixture in the reactor. The corresponding signals are transmitted through electrical wires (22) to a chart recorder (23). The recorder, in turn, prints out three curves, showing the entrance and exit DO concentrations and the SOUR of the wastewater/biomass mixture in the reactor. Also shown in FIG. 1 are electrical wire connections 24, 25 and 26 between computer (21) and each of the respective elements, pumps (2 and 6) and the mixer (9).

Example of calculation: With pure oxygen being provided at (11) (10) to the mixing tank, and assuming DO levels at the front and back ends of the spiral reactor to be 20 and 10 mg/L, respectively, plus a VSS concentration of 3 g/L and a retention time of 15 minutes in the reactor, the calculation of OUR would be: $((20-10) \text{ mg/L} \times 60 \text{ min/hr})/15 \text{ min} = 40 \text{ mg O}_2/\text{L/hr}$. The calculation of SOUR based on this data would be $((20-10) \text{ mg/L} \times 60 \text{ min/hr})/((15 \text{ min})(3 \text{ g/L})) = 13 \text{ mg O}_2/\text{g VSS/hr}$.

If the SOUR drops below a preset "reference" critical level for longer than a preset "reference" critical time period, the computer activates a warning alarm and/or diverts the influent flow to an emergency tank. When the SOUR levels return back to higher than the preset critical levels for longer than a preset critical time period, the emergency diversion is stopped, normal operation is resumed and the biological reactor starts to receive the influent flow. A critical SOUR level of 3 mg $O_2$/g VSS/hr and a critical time period of 30–60 minutes may be used. (It is recommended that close attention is paid to the organics concentration in the influent wastewater during times of low OUR levels.) It should be noted that the critical SOUR level depends on the wastewater treatment system and should be selected based on earlier tests. The control circuit of the computer also provides means for the following: 1) operation of the pumps and the mixer; and 2) entering of data (user input information), which presets the critical SOUR levels and the critical time period for starting and stopping influent flow diversion to an emergency tank e.g. in the WTP.

It should be pointed out here that the user can employ OUR, instead of SOUR, as a control parameter in the device. In such a case, VSS values need not be entered in the computer. OUR (instead of SOUR) would then be used for setting the critical preset reference values. Accordingly, the computer would calculate OURs rather than SOURs.

The development of the control circuit of the computer is in the prior art. For example, see U.S. Pat. No. 4,314,969 where designated operations and measurements are accomplished automatically under the direction of a control circuit which includes a microprocessor that operates in response to a control program.

Figure 2:
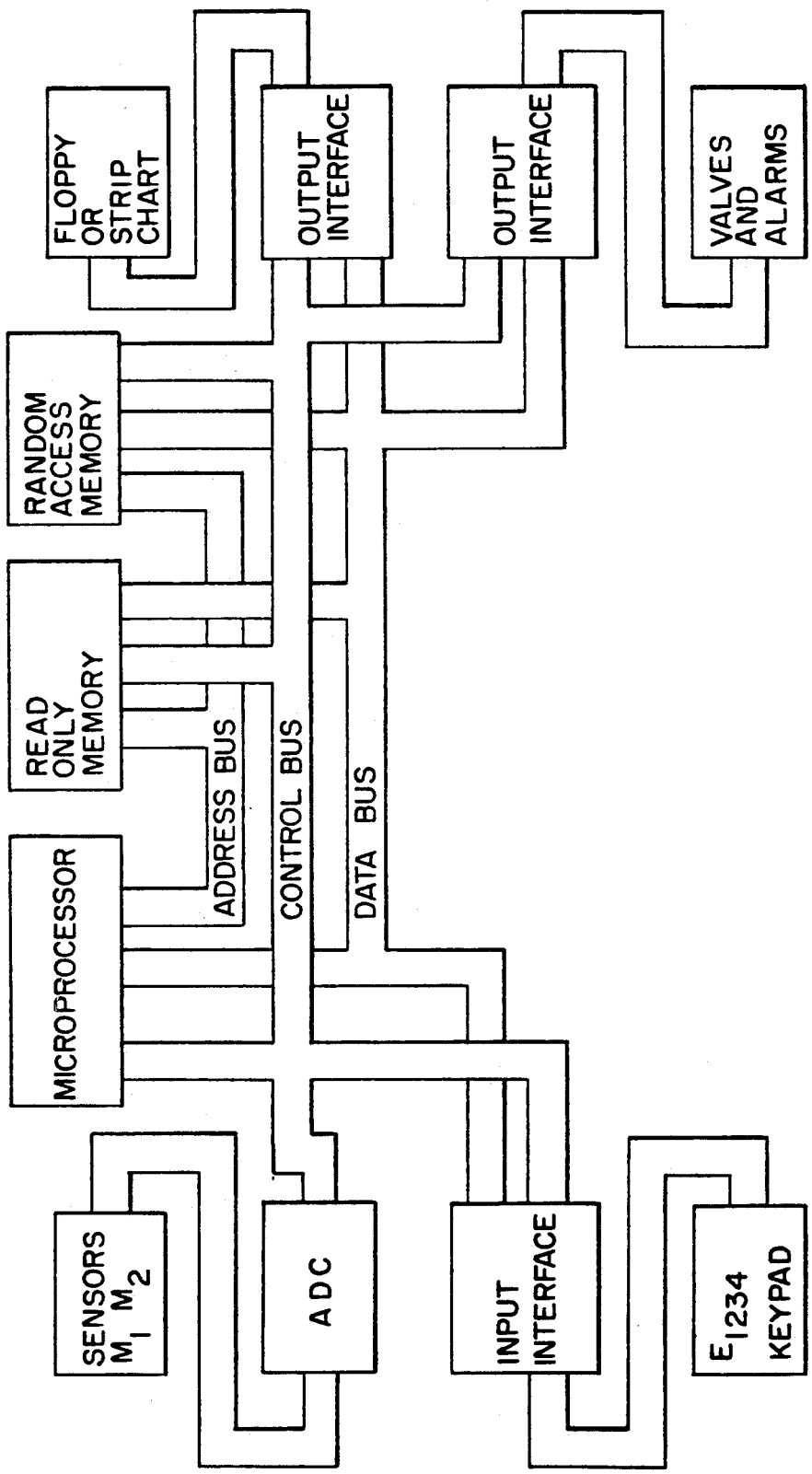
FIG. 2 shows a layout of control circuit for the computer in the device.

In FIG. 2, the layout of the control circuit is shown. An 8 bit microprocessor (Motorola 6809) is connected to the other components via address data and control buses. The 8 bit address bus serves to select devices by decoding particular address values for specific devices called device select addresses. The data bus (8 bit) is the main highway for information transfer to and from the microprocessor. The control bus (8 bit) generates the timing, synchronization, isolation and direction of data transfer for the memory and Input/Output (I/O) devices. Values for oxygen concentration (m1 and m2) are read by two analog sensors. These are fed to the system via 12 bit analog to digital converter (ADC). Note that the higher the bit number, the better is the accuracy. "Reference" values (E1, 2, 3, 4) are fed via a keyboard. The keyboard is coupled to the system via an interfacing unit. Those values are stored temporarily in random access memory (RAM). RAM is connected to the microprocessor. Results of all calculations and input values are temporarily stored here.

The results of calculations and sensor outputs are sent to a chart recorder and can also be stored on magnetic media (e.g., floppy disk). These two components are coupled to the system via an interfacing unit. Depending on the type of the chart recorder, a digital to analog converter may be necessary. The microprocessor will activate or deactivate audible and/or visual alarms and valve(s). An output module is used for interfacing. A set of triac circuits can be used for this. The microprocessor will be programmed using a machine language. The advantage of this is faster execution time. Also, programming is very flexible. Future expansions are possible.

Figure 3A:
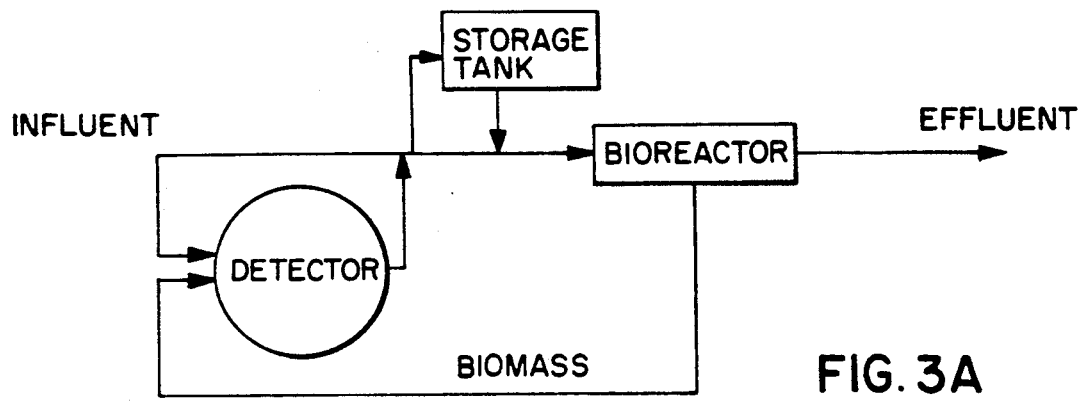

A process flow diagram showing the location of the above-described device in a WTP for use as a biological inhibition/toxicity detector is presented in FIG. 3A. The device can also be used for several other applications as follows:

(1) Apart from potential toxicity/inhibition problems caused by specific organic or inorganic compounds, the biological process performance may be adversely affected by increased loading of influent organics or by higher influent flowrates. Potential process upsets due to such phenomena can be detected through changes in SOURs monitored by the device. FIG. 3A is used for this application also.

(2) If biological treatability of a new waste stream or a new compound and/or their effect on an existing biological reactor in a WTP, is to be tested on a field pilot-scale, these can be introduced into the mixing tank either by themselves or in combination with the normal influent. A comparison of SOUR levels with the test wastestream or compound versus "control" SOUR levels would demonstrate biodegradability of the test materials or their effect on the existing WTP. FIG. 3A would be modified to be applicable for this test procedure (computer capability for activating alarm and diverting influent flow to the storage tank would not be necessary).

Figure 3B:
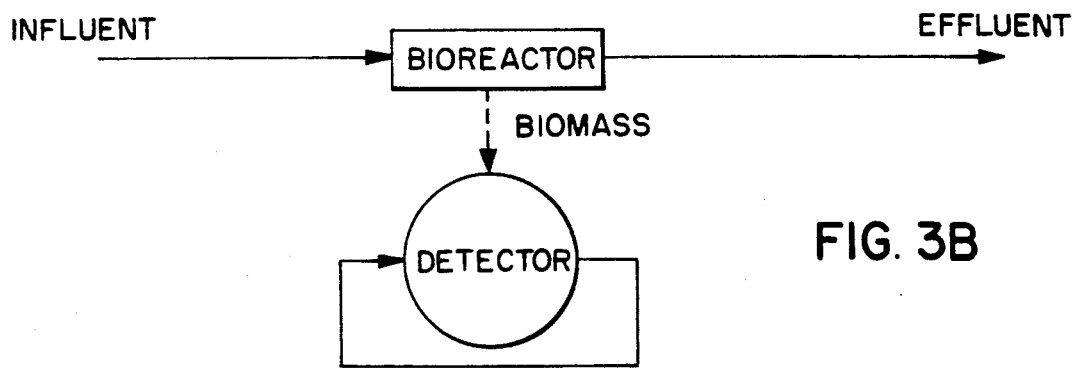

(3) "Endogenous" or background SOUR levels of acclimated active biomass, per se, can be determined by measuring SOUR of the biomass over a period of time without the influent wastewater. This can be accomplished by turning off the influent flow to the mixing tank, filling the mixing tank with the biomass containing liquid from the bioreactor and recirculating the effluent from the spiral plug flow reactor back to the mixing tank for recirculation through the reactor. Initially, the SOUR level is relatively high. However, within a few minutes, the biomass attains a sustained action, the SOUR gradually reaching a plateau indicating the endogenous level. This application is schematically shown in FIG. 3B.

Figure 3C:
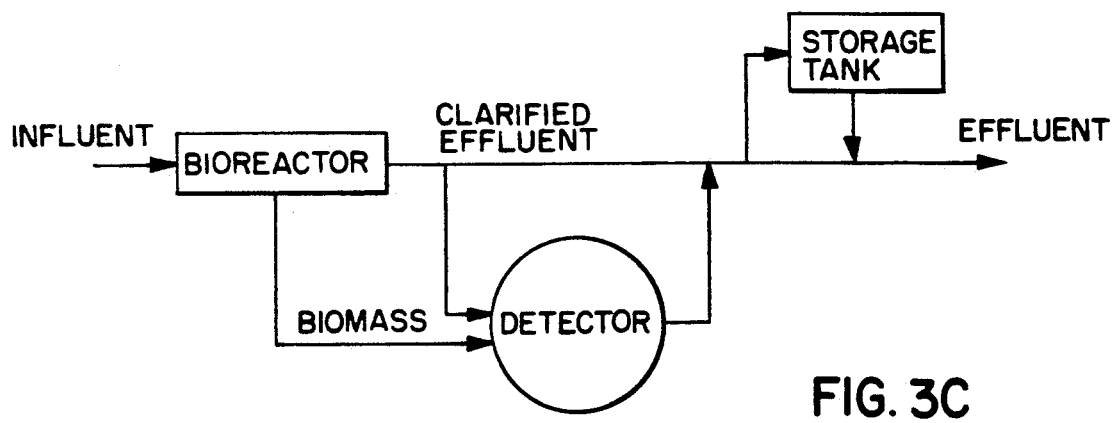

(4) Short-term specific oxygen uptake rates (SOURs) measured through the device can be historically correlated to influent or effluent $BOD_5$s. Using such correlations, influent and effluent $BOD_5$s can be estimated within 10-15 minutes instead of waiting for five days to obtain the actual $BOD_5$ results. For example, if the historical data showed a $BOD_5$ to SOUR ratio of 100, and if a SOUR of 13 mg $O_2$/g VSS/hr was measured, the $BOD_5$ of the test waste stream can be estimated to be 1,300 mg/L. FIGS. 3A and 3C will be applicable for $BOD_5$ estimates for influent and effluent, respectively. $BOD_5$ estimates for influents can be used as a process control tool to control the feed rate to biological reactors in WTPs (FIG. 3A). On the other hand, in the case of effluent $BOD_5$ estimates, potential $BOD_5$ effluent violations can be prevented or minimized by diverting the effluent to an emergency storage tank or other such measures (FIG. 3C).

I claim:

1. A biological detector device for continuously measuring the dissolved oxygen (DO) concentration and calculating the oxygen uptake rate (OUR) and/or the specific oxygen uptake rate (SOUR) of an on-line sample of wastewater and biomass (mixed liquor) or of other test liquid and biomass or of biomass, per se, continuously flowing through a simulated biological reactor which is a spiral plug-flow reactor comprising:

means for providing one or two liquids in flow communication with a mixing tank which has means for rapid mixing and means for aerating or oxygenating the liquid(s), and the mixing tank is in flow communication with a simulated biological reactor in the form of a spiral plug-flow reactor; means for continuously measuring the dissolved oxygen (DO) concentration of the oxygenated liquid as it enters and as it exits the simulated reactor and for transmitting the entrance and exit DO measurements in the form of separate electric signals through a DO analyzer(s) to electronic means adapted for processing said signals with user input data as required and therefrom calculating the OUR and/or SOUR and transmitting corresponding signals to means adapted to print out a plurality of curves showing the entrance and exit DO concentrations and the calculated OUR and/or SOUR of the liquid in the simulated reactor.

2. A device as claimed in claim 1 which is a biological inhibition/toxicity detector on-line device, which continuously calculates the OUR and/or SOUR of a mixture of an influent liquid drawn from a main line to be tested and an active biomass containing liquid, comprising:

separate means for providing two liquids in communication with the mixing tank, and the mixing tank is in communication with the plug-flow reactor; and the exit from the reactor has connecting means for return to the main influent line;

said means for continuously measuring the DO concentration and for transmitting the DO measurements in the form of separate electric signals are two dissolved oxygen (DO) probes, one located before the entrance to and the other after the exit from the plug-flow reactor;

said electronic means adapted for processing said signals with user input data as required and therefrom calculating OUR and/or SOUR and for transmitting corresponding signals is a computer electronically linked to the DO probes through a DO analyzer(s); said means adapted to print out a plurality of curves is a chart recorder electronically linked to the computer; the computer having means for processing electric signals of entrance and exit DO values and user input data of volatile suspended solids (VSS) levels and hydraulic residence time sand therefrom calculating OUR and/or SOUR of the test liquid/biomass mixture in the reactor and transmitting corresponding signals to the chart recorder, which is adapted to print out a plurality of curves showing the entrance and exit DO concentrations and the calculated OUR and/or SOUR of the test liquid/biomass mixture in the reactor, and the computer having further means for activating a warning alarm and/or means for diverting an influent flow to an emergency storage tank if OUR or SOUR drops below a preset critical level for longer than a preset critical time period and when OUR or SOUR level returns back to higher than the preset critical level for longer than a preset critical time, the computer has means to stop the diversion and restart the influent flow to its receiving system.

3. The device as claimed in claim 2, in which the computer includes means responsive to a control program for 1) operating the means for providing liquids and the mixing means in the mixing tank and 2) entering data which presets critical OUR or SOUR values, VSS levels, hydraulic residence times and critical time periods for starting and stopping an influent flow diversion to an emergency storage tank.

4. The device as claimed in claim 1, wherein the plug-flow reactor has a long, narrow, tubular configuration.

5. A biological detector device according to claim 1, which calculates the SOUR of a mixture of (i) an influent liquid to be tested by itself or in combination with normal influent and (ii) an active biomass containing liquid, comprising:

separate means for providing two liquids in communication with the mixing tank, and the mixing tank is in flow communication with the plug-flow reactor; and the exit from the reactor has connecting means for the mixture to return to its receiving system;

said means for measuring the DO concentration and for transmitting the DO measurements in the form of separate electric signals are two dissolved oxygen (DO) probes, located before the entrance to and after the exit from the plug-flow reactor;

said electronic means adapted for processing said signals with user input as required and therefrom calculating SOUR and for transmitting corresponding signals is a computer electronically linked to the DO probes through a DO analyzer(s); said means adapted to print out a plurality of curves is a chart recorder electronically linked to the computer; the computer having means for processing electric signals of entrance and exit DO values and user input data of volatile suspended solids (VSS) levels and hydraulic residence times and therefrom calculating SOUR of the test liquid/biomass mixture in the reactor and transmitting corresponding signals to the chart recorder, which is adapted to print out a plurality of curves showing the entrance and exit DO concentrations and the calculated SOUR of the test liquid/biomass mixture in the reactor.

6. The device as claimed in claim 5, in which the computer includes means responsive to a control program for 1) operating the means for providing liquids and the mixing means in the mixing tank and 2) entering data which presets VSS levels and hydraulic residence times.

7. The device as claimed in claim 5, wherein the plug-flow reactor has a long, narrow tubular configuration.

8. A biological detector device according to claim 1, which calculates the SOUR of biomass containing liquid, per se, comprising:

means for providing the liquid to the mixing tank, and the mixing tank is in flow communication with the plug-flow reactor; and the exit from the reactor has connecting means for recirculating the effluent from the plug-flow reactor back to the mixing tank for recirculation through the plug-flow reactor;

said means for measuring the DO concentration and for transmitting the measurement in the form of separate electric signals are two dissolved oxygen (DO) probes, one located before the entrance to and the other after the exit from the plug-flow reactor;

said electronic means adapted for processing said signals with user input as required and therefrom calculating SOUR and for transmitting corresponding signals is a computer electronically linked to the DO probes through a DO analyzer(s); said means adapted to print out a plurality of curves is a chart recorder electronically linked to the computer; the computer having means for processing electric signals of entrance and exit DO values and user input data of volatile suspended solids (VSS) levels and hydraulic residence times and therefrom calculating SOUR of the oxygenated biomass in the reactor and transmitting corresponding signals to the chart recorder, which is adapted to print out a plurality of curves showing the entrance and exit DO concentrations and the calculated SOUR of the oxygenated biomass in the reactor.

9. The device as claimed in claim 8, in which the the computer includes means responsive to a control program for 1) operating the means for providing the biomass liquid and the mixing means in the mixing tank and 2) entering data which presets VSS levels and hydraulic residence times.

10. The device as claimed in claim 8, wherein the plug-flow reactor has a long, narrow tubular configuration.

11. In the front end of a wastewater treatment plant (WTP) comprising an emergency storage tank and a biological system including biological reactors in which organic pollutants in the wastewater are used as food by microorganisms and converted to harmless end products, an on-line biological inhibition/toxicity detector device for continuously measuring the dissolved oxygen (DO) concentration and calculating the oxygen uptake rate (OUR) and/or the specific oxygen uptake rate (SOUR) of a mixture of influent wastewater and active biomass and thereby detecting the presence of inhibitory and toxic substances in the influent wastewater before said substances enter the system's biological reactors, said on-line device comprising:

- separate means for providing two liquids, one continuously providing a portion of the influent wastewater to a mixing tank and the other continuously providing to the same mixing tank a portion of the already acclimated active biomass from the system's biological reactors;
- said mixing tank having means for rapid mixing of the provided liquids being therein continuously combined and having oxygenated means for introducing air or oxygen from an outside source to oxygenate the liquid mixture;
- said mixing tank is in flow communication with a simulated biological reactor in the form of a spiral plug-flow reactor;
- two dissolved oxygen (DO) probes, one located before the entrance to the spiral reactor which measures the DO concentration of the wastewater/biomass mixture from the mixing tank as it enters the spiral reactor, and the other located after the exit from the spiral reactor which measures the DO concentration of the wastewater/biomass mixture as it exits the spiral reactor, each probe having a line to transmit DO values as separate electrical signals to a DO analyzer(s) connected to a computer electronically linked to the DO probes through the DO analyzer(s);
- the computer has means for processing electric signals of entrance and exit DO values and user input data of volatile suspended solids (VSS) levels and hydraulic residence times and therefrom continuously calculating the OUR and/or OUR of the wastewater/biomass mixture in the spiral reactor and transmitting corresponding signals to a chart recorder electronically linked to the computer, and the chart recorder is adapted to print out a plurality of curves showing the entrance and exit DO concentrations and the calculated OUR and/or SOUR of the wastewater/biomass mixture in the spiral reactor, and the computer has further means for activating a warning alarm and/or means for diverting the influent wastewater flow to an emergency storage tank in the front end of the WTP if OUR or SOUR drops below a preset critical value for longer than a preset critical time period, and when OUR or SOUR level returns back to higher than the preset critical level for longer than a preset critical time, the computer has means to stop the diversion and restart the influent flow to its receiving system.

12. In the device in the WTP as claimed in claim 11, the computer further including means responsive to a control program for 1) operating the means for providing liquids and the mixing means in the mixing tank and 2) entering data which presets critical OUR or SOUR values and user input VSS levels, hydraulic residence times and critical time periods for starting and stopping an influent flow diversion to an emergency storage tank in the WTP.

13. The device as claimed in claim 11, wherein the plug-flow reactor has a long, narrow tubular configuration.

14. In the back end of a wastewater treatment plant (WTP) comprising an emergency storage tank and a biological system including biological reactors in which organic pollutants in the wastewater are used as food by microorganisms and converted to harmless end products, an on-line biological detector device for continuously measuring the dissolved oxygen (DO) concentration and calculating the oxygen uptake rate (OUR) and/or the specific oxygen uptake rate (SOUR) of a mixture of clarified effluent wastewater and active biomass and thereby detecting and preventing or minimizing potential $BOD_5$ effluent violations by diversion of effluent to an emergency storage tank before effluent enters receiving waters, said on-line device comprising:

- separate means for providing tow liquids, one continuously providing a portion of the effluent wastewater to a mixing tank and the other continuously providing to the same mixing tank a portion of the already acclimated active biomass from the system's biological reactors;
- said mixing tank having means for rapid mixing of the provided liquids being therein continuously combined and having oxygenated means for introducing air or oxygen from an outside source to oxygenate the liquid mixture;
- said mixing tank is in flow communication with a simulated biological rector in the form of a spiral plug-flow reactor;
- two dissolved oxygen (DO) probes, one located before the entrance to the spiral reactor which measures the DO concentration of the wastewater/biomass mixture from the mixing tank as it enters the spiral reactor, and the other located after the exit from the spiral reactor which measures the DO concentration of the wastewater/biomass mixture as it exits the spiral reactor, each probe having a line to transmit DO values as separate electrical signals to a DO analyzer(s) connected to a computer electronically linked to the DO probes through the DO analyzer(s);
- the computer has means for processing electric signals of entrance and exit DO values and user input data of volatile suspended solids (VSS) levels and hydraulic residence times and therefrom continuously calculating the OUR and/or SOUR of the wastewater/biomass mixture in the spiral reactor and transmitting corresponding signals to a chart recorder electronically linked to the computer, and the chart recorder is adapted to print out a plurality of curves showing the entrance and exit DO concentrations and calculated OUR and/or SOUR of the wastewater/biomass mixture in the spiral reactor, and with further means for activating a warning alarm and/or means for diverting the effluent wastewater flow to an emergency storage tank in the back end of the WTP if OUR or SOUR exceeds a preset critical value for longer than a preset critical time period, and when OUR or SOUR level returns back to lower than the preset critical level for longer than a preset critical time, the computer has means to stop the diversion and restart the effluent flow to its receiving system.

15. In the device in the WTP as claimed in claim 14, the computer further including means responsive to a control program for 1) operating the means for providing liquids and the mixing means in the mixing tank and 2) entering data which presets critical OUR or SOUR values and user input VSS levels, hydraulic residence times and critical time periods for starting and stopping an effluent flow diversion to an emergency storage tank in the WTP.

16. The device as claimed in claim 14, wherein the plug-flow reactor has a long, narrow tubular configuration.

17. A method of continually estimating $BOD_5$ values of wastewater samples within brief residence time periods through historical correlations developed between short-term specific oxygen uptake rate (SOUR) measurements and historical normal $BOD_5$ values comprising steps of
  (1) providing suitable portions of an influent or effluent wastewater liquid flow to be tested and an active biomass containing liquid to a mixing tank and rapidly mixing the liquids while supplying oxygen or air from an outside source to the mixture in the tank to oxygenate the mixture,
  (2) feeding the oxygenated mixture from the mixing tank into a simulated biological reactor which is a spiral plug-flow reactor for a residence time in the spiral reactor sufficient for action of biomass on organics in the wastewater liquid of the oxygenated mixture,
  (3) making separate measurements of the dissolved oxygen (DO) concentration of the oxygenated mixture at the entrance to and at the exit from the plug-flow reactor,
  (4) transmitting each of the DO measurements in the form of separate electric signals to a DO analyzer(s) electronically linked to a computer,
  (5) in response to program control, the computer processes electric signals of entrance and exit DO measurements from the DO analyzer together with user input data of volatile suspended solids (VSS) levels and hydraulic residence times and therefrom calculates short-term SOUR level of the wastewater liquid/biomass mixture in the reactor and the computer, which is electronically linked to a chart recorder, transmits corresponding signals to the chart recorder which is adapted to print out a plurality of curves showing entrance and exit DO concentrations and the calculated SOUR of the wastewater liquid/biomass mixture in the reactor and
  (6) applying historical data of normal influent/effluent $BOD_5$s to SOUR ratios to short-term calculated SOUR measurements to obtain estimated $BOD_5$ values.

18. A method as claimed in claim 17, in which the computer has the capability to enter data which presets critical SOUR levels and critical time periods, and the capability of activating a warning alarm and/or diverting influent or effluent flow to an emergency storage tank if influent critical SOUR value drops below a preset critical level for a preset critical time period or if effluent critical SOUR value exceeds a preset critical level for a preset critical time period and the further capability of stopping the diversion and restarting the influent or effluent flow to its receiving system.

19. The method as claimed in claim 17, wherein the plug-flow reactor has a long, narrow tubular configuration.

20. A method of measuring background respiration rate of biomass, per se, from biological reactors comprising
  (1) introducing biomass containing liquid from a biological rector into a mixing tank and rapidly mixing the liquid while supplying air or oxygen from an outside source to the liquid being mixed in the tank to oxygenate the liquid,
  (2) feeding the oxygenated mixture from the mixing tank into a simulated biological reactor which is a spiral plug-flow reactor and recirculating the effluent from the spiral reactor back to the mixing tank for recirculation through the spiral reactor for a residence time sufficient for a sustained action of biomass on organics therein,
  (3) making separate measurements of the dissolved oxygen (DO) concentration of the oxygenated biomass at the entrance to and exit from the spiral plug-flow reactor,
  (4) transmitting each of the DO measurements in the form of separate electric signals to a DO analyzer(s) electronically linked to a computer,
  (5) in response to program control, the computer processes electric signals of entrance and exit DO measurements from the DO analyzer(s) together with user input data of volatile suspended solids (VSS) levels and hydraulic residence times and therefrom calculates specific oxygen uptake rate (SOUR) level of the biomass containing liquid, and the computer transmits corresponding signals to a chart recorder which is adapted to print out a plurality of curves showing entrance and exit DO concentrations and calculated SOUR of the biomass, per se.

21. The method as claimed in claim 20, wherein the plug-flow reactor has a long, narrow, tubular configuration.

22. A method for continuously measuring the dissolved oxygen (DO) concentration of a mixture of wastewater and an active biomass containing liquid in a simulated reactor and therefrom continuously calculating the oxygen utilization rate (OUR) and/or specific oxygen uptake rate (SOUR) levels of the mixture in the simulated reactor and thereby detecting and avoiding a potential process upset or detecting and avoiding or minimizing potential $BOD_5$ effluent violation comprising the steps of
  (1) continuously combining suitable portions of a wastewater liquid flow and an active biomass containing liquid in a mixing tank and rapidly mixing the liquids while supplying air or oxygen from an outside source to oxygenate the liquid mixture in the tank,
  (2) feeding the oxygenated mixture to a simulated biological reactor which is a spiral plug-flow reactor, (3) continuously measuring the DO concentration of the liquid mixture with a DO probe at the entrance to the spiral reactor and a separate DO probe at the exit from the spiral reactor and transmitting these measurements in the form of separate electric signals to a DO analyzer electronically linked to a computer which has user input data entered therein including reference values of hydraulic residence times in minutes and biomass concentration expressed as volatile suspended solids (VSS), in g/L, (4) the computer continuously calculating therefrom the OUR and/or SOUR of the mixture in the reactor and sending corresponding signals to a chart recorder electronically linked to the computer, the chart recorder printing out a plurality of curves showing entrance and exit DO concentrations and calculated OUR and/or SOUR of the mixture in the reactor, (5) the calculated OUR and/or SOUR monitoring and when the calculated OUR or SOUR level drops below or exceeds preset critical OUR or SOUR levels for preset critical time periods included as user input data entered in the computer, the computer has the capability of activating a warning alarm and/or triggering a diversion of the liquid flow to an emergency storage tank, thus detecting and avoiding potential process upsets before an influent flow reaches the actual biological reactor of the biological system or detecting and avoiding or minimizing potential $BOD_5$ effluent violations to receiving waters, and (6) when the calculated OUR or SOUR level returns to within preset critical OUR or SOUR levels for longer than a preset critical time period, the computer has the capability to stop the diversion and normal operation is resumed and the liquid flows to its receiving system.

23. A method as claimed in claim 22, wherein the calculated OUR expressed as mg of oxygen utilized/L/hour (mg $$O_2/L/hr) = \frac{(\text{entrance } DO \text{ concentration} - \text{exit } DO \text{ concentration})(60 \text{ min/hr})}{\text{hydraulic residence time}}$$

and wherein the calculated SOUR expressed as mg of oxygen $$\text{utilized}/g \ VSS/hr \ (mg \ O_2/g \ VSS/hr) = \frac{(\text{entrance } DO \text{ concentration} - \text{exit } DO \text{ concentration})(60 \text{ min/hr})}{(\text{hydraulic residence time})(g/L \ VSS)}.$$

24. The method as claimed in claim 16, wherein the plug-flow reactor has a long, narrow tubular configuration.

* * * * *